United States Patent
Davenport et al.

(10) Patent No.: US 6,383,529 B2
(45) Date of Patent: May 7, 2002

(54) PROCESS AND COMPOSITION FOR CONTROLLING FECAL HAIR EXCRETION AND TRICHOBEZOAR FORMATION

(75) Inventors: Gary Mitchell Davenport, Dayton; Gregory D. Sunvold, Eaton; Gregory A. Reinhart; Michael Griffin Hayek, both of Dayton, all of OH (US)

(73) Assignee: The Iams Company, Dayton, OH (US)

( * ) Notice: Subject to any disclaimer, the term of this patent is extended or adjusted under 35 U.S.C. 154(b) by 0 days.

(21) Appl. No.: 09/756,452

(22) Filed: Jan. 8, 2001

Related U.S. Application Data

(60) Provisional application No. 60/175,095, filed on Jan. 7, 2000.

(51) Int. Cl.$^7$ .............................. A23K 1/14; A61K 35/78
(52) U.S. Cl. ...................... 424/773; 424/725; 424/773; 424/442; 424/94.1
(58) Field of Search .................................. 424/442, 725, 424/773, 94.1, 94.65, 94.66; 514/54

(56) References Cited

U.S. PATENT DOCUMENTS

| | | | |
|---|---|---|---|
| 5,616,569 A | * | 4/1997 | Reinhart |
| 5,656,312 A | | 8/1997 | Erasmus et al. |
| 5,932,258 A | * | 8/1999 | Sunvold |
| 5,965,175 A | * | 10/1999 | Reinhart et al. |
| 6,080,403 A | * | 6/2000 | Shields, Jr. et al. |

FOREIGN PATENT DOCUMENTS

EP    0 674 842 A1    10/1995

OTHER PUBLICATIONS

Diez, Marianne et al, "Influence of a blend of fructo–oligosaccharides and sugar beet fiber on nutrient digestibility and plasma metabolite concentrations in healthy beagles," American Journal of Veterinary Research, vol. 58, No. 11, Nov. 1, 1997, pp. 1238–1242.

Diez, Marianne et al, "The influence of sugar–beet fibre, guar gum and inulin on nutrient digestibility, water consumption and plasma metabolites in healthy beagle dogs," Research in Veterinary Science, British Veterinary Association, London, vol. 64, No. 2, 1998, pp. 91–96.

Howell, S.R. et al, Prevention of Trichobezoar in the Cotton Rat, *Signodeon hispidus hispidus*, Science, vol. 107, 1948, pp. 424–425.

Drackley J.K. et al, "Energetic substrates for intestinal cells," In: Reinhart G.A. and Carey D.P., eds., Recent Advances in Canine and Feline Nutrition: vol. 2. 1998 Iams Nutrition Symposium Proceedings, Wilmington, OH; Orange Frazer Press, (1998) 463–472.

* cited by examiner

Primary Examiner—Leon B. Lankford, Jr.
Assistant Examiner—Ruth A. Davis
(74) Attorney, Agent, or Firm—Schwegman, Lundberg, Woessner & Kluth, P.A.

(57) ABSTRACT

A process and composition for controlling fecal hair excretion and trichobezoar formation in animals such as cats and rabbits is provided and includes feeding the animal a composition comprising from about 10 to about 42 wt % crude protein, from about 4 to about 30 wt % fat, from about 1 to about 25 wt % total dietary fiber, and a supplemental fiber source. The supplemental fiber source is present in amounts which provide from about 1 to about 13 weight percent of supplemental total dietary fiber. The animal is maintained on the diet for a sufficient period of time to control fecal hair excretion and trichobezoar formation.

8 Claims, No Drawings

PROCESS AND COMPOSITION FOR CONTROLLING FECAL HAIR EXCRETION AND TRICHOBEZOAR FORMATION

CROSS REFERENCE TO RELATED APPLICATIONS

This application claims the benefit of U.S. provisional application Serial No. 60/175,095, filed Jan. 7, 2000.

BACKGROUND OF THE INVENTION

The present invention relates to a process and composition for controlling fecal hair excretion and trichobezoar formation in animals such as cats and rabbits which are prone to hairball formation.

Animals that constantly groom themselves, such as cats and rabbits, regularly ingest large quantities of hair. Normally, the ingested hair passes through the gastrointestinal tract of the animal and is excreted in the feces. However, the ingestion of large quantities of hair may cause the hair to accumulate in the stomach and form a hairball or trichobezoar. A hairball is typically composed of hair, mucous, water, food particles and mineral salts. A hairball can be harmful to the animal if it impedes the normal digestive process by blocking the pylorus and preventing the passage of digesta down the gastrointestinal tract. More frequently, hairballs are nothing more than a nuisance to the animal and its owner. For example, the cat will attempt to eliminate the hairball from the stomach through the vomiting reflex. A hairball may produce constipation and defecation difficulties if it passes from the stomach and becomes lodged in the lower bowel.

Hairballs have been historically treated using petrolatum jelly, mineral oil and other laxatives contained in various forms as dietary treats and(or) supplements. The effectiveness of these laxative type compounds on hairball control has been variable at best. An alternate strategy that has been attempted to control the formation and occurrence of hairballs involves the use of diets or dietary supplements which include high levels of indigestible (insoluble) fiber such as cellulose to increase the passage of hair through the gastrointestinal tract and into the feces without causing blockage or constipation. However, such diets may decrease stool quality, cause diarrhea, and otherwise do not promote gastrointestinal health.

Although fiber is not required in the diet of animals, research has shown that moderate amounts of fermentable fibers in the diet help to maintain gastrointestinal tract health. Depending upon the specific composition and physical properties, dietary fiber generally increases water-holding capacity, controls gastric emptying, increases intestinal transit time, and maintains the structural integrity of the intestinal mucosa. However, large amounts of highly fermentable fiber sources generally decrease dry matter, protein and lipid digestibility, and may produce diarrhea-like feces, especially when fed to cats. See, Sunvold G. D. et al, "Dietary fiber for cats: In vitro fermentation of selected fiber sources by cat fecal inoculum and in vivo utilization of diets containing selected fiber sources and their blends," *J. Anim. Sci.* (1995)73:2329–2339. Other possible side effects, such as constipation, excessive stool output, decreased nutrient digestibility, and inferior haircoat appearance, have also been observed in cats fed large amounts of insoluble fiber sources.

Studies utilizing moderately fermentable (digestible) fiber sources, such as beet pulp, fructooligosaccharides (FOS), citrus pulp, and gum arabic, have been shown to increase short-chain fatty acid production, colonic cell proliferation, skin and coat quality, and stool consistency. See, Sunvold G. D. et al, supra; Drackley J. K. et al, "Energetic substrates for intestinal cells," In: Reinhart G. A. and Carey D. P., eds., *Recent Advances In Canine and Feline Nutrition: Volume 2.* 1998 *Iams Nutrition Symposium Proceedings,* Wilmington, Ohio: Orange Frazer Press, (1998) 463–472.; and Kelley, R. et al, "Effect of beet pulp on nutrient digestibility in the feline," *J. Anim. Sci.* (1998) 76 (Suppl 1):174. However, the effects of moderately fermentable fiber sources on hairball formation and fecal hair excretion have not been studied.

Accordingly, there exists a need in the art for a process and composition for controlling fecal hair excretion and trichobezoar formation in animals such as cats and rabbits which is effective and does not have the drawbacks of the prior art.

SUMMARY OF THE INVENTION

The present invention meets that need by providing a process and composition for controlling fecal hair excretion and trichobezoar formation in animals such as cats and rabbits which is effective, which promotes gastrointestinal health, and which does not cause other gastrointestinal problems in the animal. In accordance with one aspect of the present invention, a process for controlling fecal hair excretion and trichobezoar formation in an animal is provided and includes feeding the animal a composition comprising from about 10 to about 42 wt % crude protein, from about 4 to about 30 wt % fat, from about 1 to about 25 wt % total dietary fiber, and a supplemental fiber source.

The supplemental fiber source is preferably selected from the group consisting of at least one fermentable fiber; a blend of at least two fermentable fibers; a blend of at least one fermentable fiber and a cellulose ether; a blend of at least one fermentable fiber, a cellulose ether, and mineral oil; and a blend of at least one fermentable fiber and at least one non-fermentable fiber. The supplemental fiber source is preferably present in an amount which provides from about 1 to about 13 weight percent of supplemental total dietary fiber, more preferably, from about 6 to about 12 weight percent, and most preferably, from about 10 to about 12 weight percent.

By "fermentable fiber" we mean fiber sources which have an organic matter disappearance of between about 15 to about 100 percent when fermented by fecal bacteria for a 24 hour period. Preferably, the fermentable fibers used in the composition of the present invention have an organic matter disappearance of at least 20 percent. The fermentable fibers are preferably selected from the group consisting of beet pulp, gum arabic, fructooligosaccharides, and blends thereof.

By "non-fermentable fiber" we mean fiber sources which have an organic matter disappearance of less than about 15 percent when fermented by fecal bacteria for a 24 hour period.

In one embodiment of the invention, the supplemental fiber source comprises a blend of beet pulp and carboxymethylcellulose. In another embodiment, the supplemental fiber source comprises a blend of beet pulp, carboxymethylcellulose, and mineral oil. In yet another embodiment, the supplemental fiber source comprises a blend of beet pulp and cellulose.

In another embodiment of the invention, the supplemental fiber source comprises about 6 wt % beet pulp, about 2.0 wt % gum arabic, and about 1.5 wt % fructo-oligosaccharides. In another embodiment, the supplemental fiber source comprises about 6 wt % beet pulp and about 1.5 wt % carboxymethylcellulose. In another embodiment, the supplemental fiber source comprises about 6 wt % beet pulp, about 1.5 wt % carboxymethylcellulose, and about 2 wt % mineral oil. In another embodiment, the supplemental fiber source comprises about 6 wt % beet pulp, and about 6.5 wt % cellulose. In another embodiment, the supplemental fiber source comprises about 12 wt % beet pulp.

The animal is maintained on the diet for a sufficient period of time to control fecal hair excretion and trichobezoar formation.

Accordingly, it is a feature of the present invention to provide a process and composition for controlling fecal hair excretion and trichobezoar formation in animals such as cats and rabbits which is effective, which promotes gastrointestinal health, and which does not cause other gastrointestinal problems in the animal. This, and other features and advantages of the present invention, will become apparent from the following detailed description and the accompanying claims.

DETAILED DESCRIPTION OF THE PREFERRED EMBODIMENTS

The present invention provides a composition which, when fed to an animal such as a cat or rabbit which is prone to hairball formation, effectively controls the formation of hairballs and fecal hair excretion, while at the same time promotes gastrointestinal health in the animal. The present invention provides an improvement over prior treatments for hairballs such as the use of pineapple juice, hay, petrolatum, and mineral oil which function by either dissolving some of the protein in the hairball or by moving hair through the intestine. The present invention not only provides an effective method for the removal of hairballs from an animal's gastrointestinal tract, but also promotes gastrointestinal health by including blends of fermentable fibers capable of producing short chain fatty acids which promote epithelial cell health and modulate the bacterial population in the intestine.

The fermentable fibers used in the practice of the present invention display certain organic matter disappearance percentages. The fermentable fibers will have an organic matter disappearance (OMD) of from about 15 to about 100 percent when fermented by fecal bacteria in vitro for a 24 hour period. That is, from about 15 to about 100 percent of the total organic matter originally present is fermented and converted by the fecal bacteria. The organic matter disappearance of the fibers is preferably at least 20 percent, and most preferably is at least 30 percent.

Thus, in vitro OMD percentage may be calculated as follows:

$$\{1-[(\text{OM residue}-\text{OM blank})/\text{OM initial}]\}\times 100,$$

where OM residue is the organic matter recovered after 24 hours of fermentation, OM blank is the organic matter recovered in corresponding blank tubes (i.e., tubes containing medium and diluted feces, but no substrate), and OM initial is that organic matter placed into the tube prior to fermentation. Additional details of the procedure are found in Sunvold et al, J. Anim. Sci. 1995, vol. 73:1099–1109.

Fermentable fibers which are useful in the present invention produce short chain fatty acids (SCFAs) within a range of from about 28 to about 85 mmol SCFA per 1000 Calories (kcals) of metabolizable energy (ME), and more preferably within a range of from about 42 to about 71 mmol SCFA per 1000 ME kcals. This equates to a composition which has a total fermentable fiber content which yields from about 100 to about 350 mmol SCFA/kg of diet.

Millimoles of SCFAs per 1000 metabolizable energy kilocalories are calculated by first calculating the total calories of metabolizable energy (ME) in a given diet composition per kilogram of the composition. The number of grams per 1000 kcal ME may be derived from the first calculation. Then the grams, and thus millimoles, of the fermentable fiber components of the composition may be calculated.

The fermentable fibers may be any fiber source which intestinal bacteria present in the animal can ferment to produce significant quantities of SCFAs. "Significant quantities" of SCFAs, for purposes of this invention, are amounts over 0.5 mmol of total SCFAs/gram of substrate in a 24 hour period. Preferred fibers include beet pulp, gum arabic, gum talha, rice bran, carob bean gum, citrus pulp, citrus pectin, fructooligosaccharides, mannanoligosaccharides and mixtures and blends of these fibers.

The fermentable fibers may also be blended with other non-digestible fiber sources such as cellulose and cellulose ethers, or with laxatives such as petrolatum jelly or mineral oil. In a preferred embodiment, the fermentable fibers are selected from the group consisting of beet pulp, gum arabic, fructooligosaccharides, and blends thereof.

Preferably, the blend of at least one fermentable fiber and a cellulose ether includes beet pulp and carboxymethylcellulose. Preferably, the blend of at least one fermentable fiber, a cellulose ether, and mineral oil includes beet pulp, carboxymethylcellulose, and mineral oil. Preferably, the blend of at least one fermentable fiber and at least one non-fermentable fiber includes beet pulp and cellulose.

Most preferably, the supplemental fiber source is selected from the group consisting of 6 wt % beet pulp, 2.0 wt % gum arabic, and 1.5 wt % fructo-oligosaccharides; 6 wt % beet pulp and 1.5 wt % carboxymethylcellulose; 6 wt % beet pulp, 1.5 wt % carboxymethylcellulose, and 2 wt % mineral oil; 6 wt % beet pulp and 6.5 wt % cellulose; and 12 wt % beet pulp.

The fermentable fibers are used in the pet food composition in amounts which provide from about 1 to about 13 weight percent of supplemental total dietary fiber, preferably from about 6 to about 12 weight percent, and most preferably from about 10 to about 12 weight percent.

A definition of "supplemental total dietary fiber" first requires an explanation of "total dietary fiber". "Total dietary fiber" is defined as the residue of plant food which is resistant to hydrolysis by animal digestive enzymes. The main components of total dietary fiber are cellulose, hemicellulose, pectin, lignin and gums (as opposed to "crude fiber", which only contains some forms of ellulose and lignin). "Supplemental total dietary fiber" is that dietary fiber which is added to a food product above and beyond any dietary fiber naturally present in other components of the food product. Also, a "fiber source" is considered such when it consists predominantly of fiber.

The animal is preferably fed a diet comprising from about 10 to about 42 wt % crude protein, from about 4 to about 30 wt % fat, from about 1 to about 25 wt % total dietary fiber, with from about 1 to about 13 wt % of supplemental total dietary fiber as described above. Other vitamins, minerals, and nutrients may also be present.

The use of fermentable fiber sources has proved to be beneficial for controlling hairballs by increasing the gastric and intestinal passage of ingested hair and their subsequent excretion in the feces of the animal. While not wishing to be bound by any particular theory, it is believed that the increased passage rate and fecal excretion reduce the opportunity for hair to collect in the gastrointestinal tract of the animal and form a hairball. Thus, it is believed that a viscous fiber source, such as a fermentable fiber alone or blended with other fibers, traps or binds the ingested hair to food particulate matter. The increased fiber level increases gastric emptying, allowing the hair to pass out through the feces of the animal more frequently. This increased passage frequency is believed to decrease the accumulation of hair in the stomach and the chronic formation of hairballs. An additional benefit of a supplemental fermentable fiber source is the enhancement of overall digestion by ensuring adequate time for digestion, thus preventing any nutritional deficiencies. In contrast, the use of insoluble fiber as the sole fiber source in feline diets may cause detrimental effects on nutrient digestibility and stool quality and may negatively impact skin and coat condition when fed for an extended period of time.

In order that the invention may be more readily understood, reference is made to the following examples, which are intended to be illustrative of the invention, but are not intended to be limiting in scope.

EXAMPLE 1

A number of dietary compositions were tested for their effect on fecal hair excretion and prevention of the formation of hairballs in the gastrointestinal tract. The potential efficacy of dietary fiber sources for controlling hairball formation was evaluated by assessing the degree of fecal hair excretion and hair shedding. The fiber sources were evaluated by incorporating them into various dietary matrices containing chicken, poultry meal, ground corn, grain sorghum, egg, fishmeal, poultry fat, vitamins and minerals. The fiber sources and(or) blends that were evaluated were: (1) 6 wt % beet pulp, 2.0 wt % gum arabic, and 1.5 wt % fructo-oligosaccharides (FOS); (2) 6 wt % beet pulp and 1.5 wt % carboxymethylcellulose; (3) 6 wt % beet pulp, 1.5 wt % carboxymethylcellulose, and 2 wt % mineral oil; (4) 6 wt % beet pulp and 6.5% cellulose; and (5) 12% beet pulp. Control diets that were used for comparative purposes included: a dietary matrix with 13 wt % cellulose added as the fiber source and a commercially available cat food formulation containing approximately 4 wt % beet pulp.

These five experimental diets and two control diets were evaluated by feeding to 80 cats during a 10-week feeding study. The study was comprised of a 6-week baseline period and a 4-week experimental period. During the baseline period, all cats were fed the commercially available cat food formulation to establish baseline shedding and fecal hair excretion rates for the individual cats. These results were used to allot the cats to the eight diets to standardize hair shedding and fecal hair excretion across the eight diets. Criteria used to assess efficacy of the various fiber sources and(or) blends were based on subjective stool scores (score of 4.0 being ideal), shedding index, wet feces, fecal moisture content, dry feces, and daily fecal hair excretion.

Fecal excreta was collected from each cat on a weekly basis during the experimental period to assess fecal hair content. The composited weekly sample for each cat was freeze-dried and ground before the hair component was quantitatively separated using a series of screens and mechanical tapping. A shedding index was assigned for each cat by collecting and weighing hair produced when a standardized brushing protocol was followed.

Test results are reported in Tables 1 through 6 below. As can be seen from Table 2, cats consuming Diet #3 exhibited significantly reduced shedding by the fourth week.

TABLE 1

Subjective stool scores
(1 = liquid, watery; 2 = liquid, gel; 3 = semi-formed;
4 = formed; 5 = hard, dry)

| Diet | Fiber source | Baseline | Week 1 | Week 2 | Week 3 | Week 4 |
|---|---|---|---|---|---|---|
| 1 | 6% Beet pulp, 2% gum arabic, 1.5% FOS | 4.22 | 4.03 | 3.97 | 4.10 | 3.86 |
| 2 | 6% Beet pulp, 1.5% carboxymethylcellulose | 3.89 | 3.75 | 3.62 | 3.49 | 3.67 |
| 3 | 6% Beet pulp, 1.5% carboxymethylcellulose 2% mineral oil | 4.34 | 4.14 | 4.27 | 4.21 | 4.13 |
| 4 | 6% Beet pulp, 6.5% cellulose | 4.43 | 4.59 | 4.57 | 4.57 | 4.64 |
| 5 | 12% Beet pulp | 4.34 | 4.49 | 4.48 | 4.48 | 4.60 |
| 6 | 13% Cellulose | 4.31 | 4.57 | 4.55 | 4.59 | 4.55 |
| 7 | Commercial Cat Food Formulation | 4.34 | 3.90 | 4.02 | 4.09 | 4.21 |

TABLE 2

Shedding index (grams hair collected following brushing)

| Diet | Fiber source | Baseline | Week 4 | Time Effect (P<) |
|---|---|---|---|---|
| 1 | 6% Beet pulp, 2% gum arabic, 1.5% FOS | .56 | .41 | |
| 2 | 6% Beet pulp, 1.5% carboxymethylcellulose | .44 | .42 | |
| 3 | 6% Beet pulp, 1.5% carboxymethylcellulose, 2% mineral oil | $.53^x$ | $.25^y$ | .05 |
| 4 | 6% Beet pulp, 6.5% cellulose | .39 | .28 | |
| 5 | 12% Beet pulp | .58 | .46 | |
| 6 | 13% Cellulose | .40 | .36 | |
| 7 | Commercial Cat Food Formulation | .31 | .27 | |
| | Diet Effect (P<) | | NS | |

TABLE 3

Wet feces (grams/day)

| | Baseline | | | Week 1 | | | | | | Week 2 | | | Week 3 | | | Week 4 | | | Time |
| --- | --- | --- | --- | --- | --- | --- | --- | --- | --- | --- | --- | --- | --- | --- | --- | --- | --- | --- | --- |
| | | | | Days 1–3 | | | Days 4–7 | | | | | | | | | | | | |
| | g/d | diet | time | 1–3 | diet | time | 4–7 | diet | time | g/d | diet | time | g/d | diet | time | g/d | diet | time | (p <) |
| Beet Pulp (6%) + gum arabic (2%) + FOS (1.5%) | 31.62 | | | 28.97 | ab | | 40.06 | ab | | 42.76 | | | 40.03 | ab | | 41.40 | ab | | NS |
| Beet pulp (6%) + carboxy-methyl-cellulose (1.5%) | 32.12 | | x | 53.55 | c | y | 46.31 | b | y | 42.78 | | x | 46.88 | b | y | 43.29 | ab | | 0.05 |
| Beet pulp (6%) + carboxy-methyl-cellulose (1.5%) + mineral oil (2%) | 31.47 | | | 40.26 | b | | 31.73 | ab | | 33.39 | | | 37.97 | ab | | 42.11 | ab | | NS |
| Beet pulp (6%) + cellulose (6.5%) | 39.03 | | | 39.79 | ab | | 41.87 | ab | | 42.23 | | | 41.94 | ab | | 48.01 | a | | NS |
| Beet pulp (12%) | 34.16 | | x | 56.07 | c | y | 41.44 | ab | x | 41.67 | | x | 43.35 | ab | xy | 44.42 | ab | | 0.05 |
| Cellulose (13%) | 35.03 | | | 28.23 | a | | 38.50 | ab | | 35.83 | | | 36.55 | ab | | 37.96 | ab | | NS |
| Commercial Cat Food Formulation | 32.41 | | | 38.65 | ab | | 36.32 | ab | | 34.28 | | | 34.40 | a | | 35.91 | ab | | NS |
| Diet (P <) | | NS | | | 0.10 | | | 0.05 | | | NS | | | 0.10 | | | 0.05 | | | a, b, c Means in the same column with different superscripts are statistically different (P < 0.05).
x, y Means in the same row with different superscripts are statistically different (P < 0.05).

TABLE 4

Fecal moisture content (%)

| | Baseline | | | Week 1 | | | | | | Week 2 | | | Week 3 | | | Week 4 | | | Time |
| --- | --- | --- | --- | --- | --- | --- | --- | --- | --- | --- | --- | --- | --- | --- | --- | --- | --- | --- | --- |
| | | | | Days 1–3 | | | Days 4–7 | | | | | | | | | | | | |
| | % | diet | time | 1–3 | diet | time | 4–7 | diet | time | % | diet | time | % | diet | time | % | diet | time | (p <) |
| Beet Pulp (6%) + gum arabic (2%) + FOS (1.5%) | 61.9 | | x | 66.2 | bc | xy | 67.9 | c | y | 68.3 | bc | y | 67.83 | b | y | 67.1 | bc | | 0.10 |
| Beet pulp (6%) + carboxy-methyl-cellulose (1.5%) | 61.7 | | x | 69.2 | c | y | 70.6 | c | y | 69.3 | c | y | 68.44 | b | y | 68.6 | c | | 0.10 |
| Beet pulp (6%) + carboxy-methyl-cellulose (1.5%) + mineral oil (2%) | 61.0 | | | 61.9 | b | | 63.4 | bc | | 62.4 | b | | 65.53 | b | | 65.2 | bc | | NS |

TABLE 4-continued

Fecal moisture content (%)

| | Baseline | | | Week 1 | | | | | | Week 2 | | | Week 3 | | | Week 4 | | | Time |
|---|---|---|---|---|---|---|---|---|---|---|---|---|---|---|---|---|---|---|---|
| | | | | Days 1–3 | | | Days 4–7 | | | | | | | | | | | | |
| | % | diet | time | % | diet | time | % | diet | time | % | diet | time | % | diet | time | % | diet | time | (p <) |
| Beet pulp (6%) + cellulose (6.5%) | 60.1 | | | 62.0 | b | | 60.2 | b | | 63.1 | b | | 62.81 | b | | 62.0 | b | | NS |
| Beet pulp (12%) | 62.4 | | x | 68.0 | bc | xy | 69.5 | c | y | 69.5 | c | y | 68.45 | b | y | 68.2 | c | | 0.10 |
| Cellulose (13%) | 62.8 | | x | 52.7 | a | y | 53.80 | a | y | 51.7 | a | y | 52.76 | a | y | 51.0 | a | | 0.01 |
| Commercial Cat Food Formulation | 61.1 | | x | 66.7 | bc | xy | 67.4 | c | y | 66.0 | bc | xy | 61.96 | b | | 66.0 | bc | | 0.10 |
| Diet (P <) | | NS | | | 0.10 | | | 0.10 | | | 0.10 | | | 0.05 | | | 0.10 | | | a, b, c Means in the same column with different superscripts are statistically different (P < 0.05).
x, y Means in the same row with different superscripts are statistically different (P < 0.05).

TABLE 5

Dry feces (grams/day)

| | Baseline | | | Week 1 | | | | | | Week 2 | | | Week 3 | | | Week 4 | | | Time |
|---|---|---|---|---|---|---|---|---|---|---|---|---|---|---|---|---|---|---|---|
| | | | | Days 1–3 | | | Days 4–7 | | | | | | | | | | | | |
| | g/d | diet | time | g/d | diet | time | g/d | diet | time | g/d | diet | time | g/d | diet | time | g/d | diet | time | (p <) |
| Beet Pulp (6%) + gum arabic (2%) + FOS (1.5%) | 10.72 | ab | | 9.50 | a | | 12.43 | ab | | 12.99 | ab | | 12.32 | a | | 12.85 | bc | | NS |
| Beet pulp (6%) + carboxy-methyl-cellulose (1.5%) | 10.38 | ab | x | 15.54 | bc | y | 13.03 | ab | y | 12.17 | ab | x | 13.94 | b | y | 12.65 | bc | | 0.10 |
| Beet pulp (6%) + carboxy-methyl-cellulose (1.5%) + mineral oil (2%) | 11.19 | ab | x | 14.49 | bc | y | 10.92 | a | x | 11.09 | a | x | 12.71 | a | xy | 13.69 | bc | | 0.10 |
| Beet pulp (6%) + cellulose (6.5%) | 13.51 | a | | 13.82 | bc | | 15.24 | b | | 15.08 | bc | | 14.76 | b | | 17.34 | a | | NS |
| Beet pulp (12%) | 11.33 | ab | x | 16.33 | c | y | 12.27 | ab | x | 12.13 | ab | x | 13.39 | a | xy | 13.29 | bc | | 0.05 |
| Cellulose (13%) | 11.46 | ab | x | 12.72 | b | x | 16.88 | c | y | 16.95 | c | y | 16.42 | b | y | 17.55 | a | | 0.05 |
| Commercial Cat Food Formulation | 11.13 | ab | | 12.22 | ab | | 11.50 | ab | | 11.15 | a | | 8.30 | | | 11.72 | c | | NS |
| Diet (P <) | | 0.10 | | | 0.10 | | | 0.05 | | | 0.05 | | | 0.10 | | | 0.10 | | | a, b, c Means in the same column with different superscripts are statistically different (P < 0.05).
x, y Means in the same row with different superscripts are statistically different (P < 0.05).

TABLE 6

Daily fecal hair excretion
(separated hair fraction subjected to modified crude)

|  | Baseline | | | Week 2 | | | Week 3 | | | Week 4 | | | Overall Mean | | | Time |
|---|---|---|---|---|---|---|---|---|---|---|---|---|---|---|---|---|
|  | g/d | diet | time | g/d | diet | time | g/d | diet | time | g/d | diet | time | g/d | diet | diet | (p <) |
| Beet Pulp (6%) + gum arabic (2%) + FOS (1.5%) | 0.097 | | x | 0.126 | c | x | 0.216 | b | y | 0.082 | c | x | 0.141 | cd | de | 0.10 |
| Beet pulp (6%) + carboxymethylcellulose (1.5%) | 0.142 | | | 0.177 | c | | 0.207 | b | | 0.154 | bc | | 0.180 | bcd | cd | NS |
| Beet pulp (6%) + carboxymethylcellulose (1.5%) + mineral oil (2%) | 0.088 | | x | 0.313 | ab | y | 0.237 | b | y | 0.186 | ab | y | 0.245 | b | bc | 0.05 |
| Beet pulp (6%) + cellulose (6.5%) | 0.111 | | | 0.204 | bc | | 0.170 | bc | | 0.185 | b | | 0.186 | bc | bcd | NS |
| Beet pulp (12%) | 0.103 | | | 0.142 | c | | 0.124 | c | | 0.130 | bc | | 0.132 | cd | de | NS |
| Cellulose (13%) | 0.083 | | x | 0.369 | a | y | 0.433 | a | y | 0.260 | a | y | 0.353 | a | a | 0.01 |
| Commercial Cat Food Formulation | 0.097 | | | 0.105 | c | | 0.095 | c | | 0.105 | bc | | 0.101 | d | e | NS |
| Diet (P <) | | NS | | | 0.10 | | | 0.10 | | | 0.10 | | | 0.05 | 0.08 | | a, b, c Means in the same column with different superscripts are statistically different (P < 0.05).
x, y Means in the same row with different superscripts are statistically different (P < 0.05).

EXAMPLE 2

A second study was conducted using the same evaluation method as in Example 1 with regard to a fiber blend of 6% beet pulp and 6% cellulose incorporated in a dietary matrix containing chicken, poultry meal, ground corn, grain sorghum, egg, fishmeal, poultry fat, vitamins and minerals. A commercially available cat food formulation containing approximately 4% beet pulp was included for comparative purposes.

The results are shown in Tables 7 to 12 below.

TABLE 7

Subjective stool scores
(1 = liquid, watery; 2 = liquid, gel; 3 = semi-formed; 4 = formed; 5 = hard, dry)

| Diet | Fiber source | Baseline | | | Week 1 | | | Week 2 | | | Week 3 | | | Time Effect (P <) |
|---|---|---|---|---|---|---|---|---|---|---|---|---|---|---|
| | | SS | diet | time | SS | diet | time | SS | diet | time | SS | diet | time | |
| 1 | 6% Beet pulp, 6% cellulose | 3.95 | | x | 3.90 | | x | 4.35 | | y | 4.03 | | xy | 0.10 |
| 2 | Commercial Cat Food Formulation | 4.17 | | | 3.99 | | | 4.04 | | | 4.10 | | | NS |
| | Diet Effect (P <) | | NS | | | NS | | | NS | | | NS | | |

TABLE 8

Shedding Index (grams hair collected following brushing)

| Diet | Fiber source | Baseline g | diet | Overall Mean (w/covariate) g | diet | Time |
|---|---|---|---|---|---|---|
| 1 | 6% Beet pulp, 6% cellulose | 0.401 | a | 0.475 | | NS |
| 2 | Commercial Cat Food Formulation | 0.283 | b | 0.461 | | NS |
| | Diet Effect (P<) | | 0.01 | | NS | |

TABLE 9

Wet feces (grams/day)

| | Baseline | | | Week 1 | | | Week 2 | | | Week 3 | | | Time |
|---|---|---|---|---|---|---|---|---|---|---|---|---|---|
| | g/d | diet | time | g/d | diet | time | g/d | diet | time | g/d | diet | time | (p <) |
| 6% Beet pulp, 6% cellulose | 20.5 | | x | 32.7 | a | y | 28.2 | a | y | 33.1 | a | y | 0.01 |
| Commercial Cat Food Formulation | 16.6 | | | 16.6 | b | | 43.7 | b | | 13.7 | b | | NS |
| Diet (P <) | | NS | | | 0.01 | | | 0.01 | | | 0.01 | | | a, b, c Means in the same column with different superscripts are statistically different (P < 0.05).
x, y Means in the same row with different superscripts are statistically different (P < 0.05).

TABLE 10

Fecal moisture content (%)

| | Baseline | | | Week 1 | | | Week 2 | | | Week 3 | | | Time |
|---|---|---|---|---|---|---|---|---|---|---|---|---|---|
| | % | diet | time | % | diet | time | % | diet | time | % | diet | time | (p <) |
| 6% Beet pulp, 6% cellulose | 60.8 | a | x | 59.9 | | x | 54.4 | | y | 59.6 | | x | 0.05 |
| Commercial Cat Food Formulation | 54.1 | b | | 56.0 | | | 57.6 | | | 54.7 | | | NS |
| Diet (P <) | | 0.05 | | | NS | | | NS | | | NS | | | a, b, c Means in the same column with different superscripts are statistically different (P < 0.05).
x, y Means in the same row with different superscripts are statistically different (P < 0.05).

TABLE 11

Dry feces (grams/day)

| | Baseline | | | Week 1 | | | Week 2 | | | Week 3 | | | Time |
|---|---|---|---|---|---|---|---|---|---|---|---|---|---|
| | g/d | diet | time | g/d | diet | time | g/d | diet | time | g/d | diet | time | (p <) |
| 6% Beet pulp, 6% cellulose | 7.88 | | x | 12.05 | a | y | 12.41 | a | y | 13.06 | a | y | 0.01 |
| Commercial Cat | 7.16 | | | 6.88 | b | | 6.43 | b | | 6.02 | b | | NS |

TABLE 11-continued

|  | Dry feces (grams/day) | | | | | | | | | | | Time |
|---|---|---|---|---|---|---|---|---|---|---|---|---|
|  | Baseline | | | Week 1 | | | Week 2 | | | Week 3 | | |
|  | g/d | diet | time | g/d | diet | time | g/d | diet | time | g/d | diet | time | (p <) |
| Food Formulation Diet (P <) |  | NS |  |  | 0.01 |  |  | 0.01 |  |  | 0.01 |  | a, b, c Means in the same column with different superscripts are statistically different (P < 0.05).
x, y Means in the same row with different superscripts are statistically different (P < 0.05).

TABLE 12

Daily fecal hair excretion
(separated hair fraction subjected to modified crude)

|  | Baseline | | | Week 1 | | | Week 2 | | | Week 3 | | | Time |
|---|---|---|---|---|---|---|---|---|---|---|---|---|---|
|  | g/d | diet | time | g/d | diet | time | g/d | diet | time | g/d | diet | time | (p <) |
| 6% Beet pulp, 6% cellulose | 0.084 |  | x | 0.107 |  | x | 0.191 | a | y | 0.256 | a | z | 0.01 |
| Commercial Cat Food Formulation | 0.047 |  |  | 0.081 |  |  | 0.099 | b |  | 0.095 | b |  | NS |
| Diet (P <) |  | NS |  |  | NS |  |  | 0.01 |  |  | 0.01 |  |  | a, b, c Means in the same column with different superscripts are statistically different (P < 0.05).

As can be seen, cats consuming the diet containing 6% beet pulp and 6% cellulose exhibited increased hair excretion.

While certain representative embodiments and details have been shown for purposes of illustrating the invention, it will be apparent to those skilled in the art that various changes in the methods and apparatus disclosed herein may be made without departing from the scope of the invention.

What is claimed is:

1. A composition for controlling fecal hair excretion and trichobezoar formation in an animal comprising from about 10 to about 42 wt % crude protein from about 4 to about 30 wt % fat, from about 1 to about 25 wt % total dietary fiber, and a supplemental fiber source selected from the group consisting of a blend of at least one fermentable fiber and a cellulose ether, and a blend of at least one fermentable fiber, a cellulose ether, and mineral oil.

2. The composition of claim 1 wherein said supplemental fiber source is present in an amount which provides from about 6 to about 12 weight percent of supplemental total dietary fiber.

3. The composition of claim 1 wherein said supplemental fiber source is present in an amount which provides from about 10 to about 12 weight percent of supplemental total dietary fiber.

4. The composition of claim 1 wherein said fermentable fibers have an organic matter disappearance of at least 20 percent.

5. The composition of claim 1 wherein said supplemental fiber source comprises a blend of beet pulp and carboxyethylcellulose.

6. The composition of claim 1 wherein said supplemental fiber source comprises a blend of beet pulp, carboxymethylcellulose, and mineral oil.

7. The composition of claim 1 wherein said supplemental fiber source comprises about 6 wt % beet pulp and about 1.5 wt % carboxymethylcellulose.

8. The composition of claim 1 wherein said supplemental fiber source comprises about 6 wt % beet pulp and about 1.5 wt % carboxymethylcellulose, and about 2 wt % mineral oil.

* * * * *

UNITED STATES PATENT AND TRADEMARK OFFICE
CERTIFICATE OF CORRECTION

PATENT NO. : 6,383,529 B2  Page 1 of 1
DATED : May 7, 2002
INVENTOR(S) : Gary Mitchell Davenport, Gregory D. Sunvold, Gregory A. Reinhart and Michael Griffin Hayek It is certified that error appears in the above-identified patent and that said Letters Patent is hereby corrected as shown below:

<u>Title page,</u>
Item [56], References Cited, OTHER PUBLICATIONS, delete ";" and insert -- : --, therefor.

<u>Column 15,</u>
Line 46, delete "," after "ether" and insert -- ; --, therefor.

<u>Column 16,</u>
Line 39, delete "carboxyethylcellulose" and insert -- carboxymethylcellulose --, therefor.

Signed and Sealed this

Fifteenth Day of October, 2002

*Attest:*

JAMES E. ROGAN
*Director of the United States Patent and Trademark Office*

*Attesting Officer*